(12) United States Patent
Teramoto et al.

(10) Patent No.: US 10,906,868 B2
(45) Date of Patent: Feb. 2, 2021

(54) METHOD FOR PURIFYING N-(ALPHA-ALKOXYETHYL)FORMAMIDE, METHOD FOR PRODUCING HIGH-PURITY N-(ALPHA-ALKOXYETHYL)FORMAMIDE, AND DEVICE FOR PURIFYING N-(ALPHA-ALKOXYETHYL)FORMAMIDE

(71) Applicant: Mitsubishi Chemical Corporation, Chiyoda-ku (JP)

(72) Inventors: Kouji Teramoto, Tokyo (JP); Hitoshi Nishimura, Tokyo (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 0 days.

(21) Appl. No.: 16/390,132

(22) Filed: Apr. 22, 2019

(65) Prior Publication Data

US 2019/0241503 A1    Aug. 8, 2019

Related U.S. Application Data

(63) Continuation of application No. PCT/JP2017/044166, filed on Dec. 8, 2017.

(30) Foreign Application Priority Data

Dec. 9, 2016 (JP) ................................. 2016-239488

(51) Int. Cl.
C07C 231/24 (2006.01)
B01D 3/14 (2006.01)
(Continued)

(52) U.S. Cl.
CPC ............ *C07C 231/24* (2013.01); *B01D 3/009* (2013.01); *B01D 3/143* (2013.01); *B01D 3/26* (2013.01); *C07C 233/18* (2013.01)

(58) Field of Classification Search
CPC ..... C07C 231/24; C07C 233/18; B01D 3/009; B01D 3/26; B01D 3/143
See application file for complete search history.

(56) References Cited

U.S. PATENT DOCUMENTS 5,365,011 A 11/1994 Ramachandran et al.
5,574,185 A 11/1996 Sato et al.
(Continued)

FOREIGN PATENT DOCUMENTS

CA    1 138 884    1/1983
CA    1 249 600    1/1989
(Continued)

OTHER PUBLICATIONS

Knapp, J.P. et al. (1992) Industrial & Engineering Chemistry Research, 31(1), 346-357.*

(Continued)

*Primary Examiner* — Brian A McCaig
(74) *Attorney, Agent, or Firm* — Oblon, McClelland, Maier & Neustadt, L.L.P.

(57) ABSTRACT

A method for purifying an N-(α-alkoxyethyl)formamide contained in a mixture thereof with a plurality of distillation columns, the plurality of distillation columns being arranged serially, the method including condensing a distillate from the second or any later-stage distillation column to obtain a condensate and returning at least some of the condensate to the preceding distillation column.

11 Claims, 1 Drawing Sheet

(51) Int. Cl.
  *B01D 3/26* (2006.01)
  *C07C 233/18* (2006.01)
  *B01D 3/00* (2006.01)

(56) References Cited

U.S. PATENT DOCUMENTS

| | | |
|---|---|---|
| 5,679,872 A | 10/1997 | Streicher |
| 6,488,817 B1 | 12/2002 | Swain et al. |

FOREIGN PATENT DOCUMENTS

| | | |
|---|---|---|
| EP | 0 490 349 A2 | 6/1992 |
| EP | 0 572 239 A1 | 12/1993 |
| JP | 50-058014 | 5/1975 |
| JP | 56-075464 | 6/1981 |
| JP | 57-002239 | 1/1982 |
| JP | 61-286357 | 12/1986 |
| JP | 62-289549 | 12/1987 |
| JP | 63-017892 | 1/1988 |
| JP | 63-190862 | 8/1988 |
| JP | 63-227538 | 9/1988 |
| JP | 05-039231 | 2/1993 |
| JP | 06-079123 | 3/1994 |
| JP | 06-122661 | 5/1994 |
| JP | 06-179644 | 6/1994 |
| JP | 06-184071 | 7/1994 |
| JP | 06-279376 | 10/1994 |
| JP | 06-287232 | 10/1994 |
| JP | 07-304703 | 11/1995 |
| JP | 2002-509899 | 4/2002 |
| JP | 2010-138169 | 6/2010 |
| WO | WO 99/50208 A1 | 10/1999 |

OTHER PUBLICATIONS

International Search Report dated Mar. 6, 2018 in PCT/JP2017/044166 filed on Dec. 8, 2017 (with English Translation).

Cheol-Yi, U., et al., "Synthesis of N-α-methoxyethylformamide" Chemistry and Chemical Engineering Issued by the Science and Technology Publishing House No. 3, 2011, pp. 1-7. (with English Translation).

Extended European Search Report dated Oct. 17, 2019 in corresponding European Patent Application No. 17879134.9 citing documents AA-AC therein, 6 pages.

* cited by examiner

METHOD FOR PURIFYING N-(ALPHA-ALKOXYETHYL)FORMAMIDE, METHOD FOR PRODUCING HIGH-PURITY N-(ALPHA-ALKOXYETHYL)FORMAMIDE, AND DEVICE FOR PURIFYING N-(ALPHA-ALKOXYETHYL)FORMAMIDE

This application is a continuation application of International Application No. PCT/JP2017/044166, filed on Dec. 8, 2017, which claims the benefit of priority of the prior Japanese Patent Application No. 2016-239488 filed in Japan on Dec. 9, 2016, the entire contents of which are incorporated herein by reference.

TECHNICAL FIELD

The present invention relates to a method for purifying N-(α-alkoxyethyl)formamide, a method for producing high-purity N-(α-alkoxyethyl)formamide, and a device for purifying N-(α-alkoxyethyl)formamide.

BACKGROUND ART

N-(α-alkoxyethyl)formamide is an important substance as an intermediate raw material for N-vinylformamide.

N-(α-alkoxyethyl)formamide is obtained by, for example, reacting (alkoxylation reaction) N-(α-hydroxyethyl)formamide to be obtained by reacting (hydroxylation reaction) formamide with acetaldehyde with an alcohol in the presence of an acid catalyst.

The N-(α-alkoxyethyl)formamide thus obtained contains the solvent (reaction solvent) used in the hydroxylation reaction, water formed by the alkoxylation reaction, the excess alcohol which has not been consumed in the alkoxylation reaction, and the residue of the reaction catalyst used in the previous step. Hence, the N-(α-alkoxyethyl)formamide is usually purified by distillation to remove the reaction solvent, water, alcohol, and the like (see, for example, Patent Document 1).

CITATION LIST

Patent Document

Patent Document 1: JP 6-279376 A

SUMMARY OF THE INVENTION

Problem to be Solved by the Invention

However, the recovery rate is not necessarily sufficiently high in the conventional method for purifying N-(α-alkoxyethyl)formamide. Moreover, it is required to select a condition so as to diminish the decomposition loss at the time of purification since the thermal stability of N-(α-alkoxyethyl)formamide before purification is low.

The invention has been made in view of the above circumstances, and an object thereof is to provide a method for purifying N-(α-alkoxyethyl)formamide by which N-(α-alkoxyethyl)formamide can be purified at a high recovery rate, a method for producing high-purity N-(α-alkoxyethyl) formamide, and a device for purifying N-(α-alkoxyethyl) formamide.

Means for Solving Problem

The invention has the following aspects.

[1] A method for purifying N-(α-alkoxyethyl)formamide from a mixture containing the N-(α-alkoxyethyl)formamide by using a plurality of distillation columns, in which the plurality of distillation columns are disposed in series, and the method includes:

condensing an overhead efflux of a distillation column at a subsequent stage to obtain a condensate; and returning at least a part of the condensate to a distillation column at a preceding stage.

[2] The method for purifying N-(α-alkoxyethyl)formamide according [1], in which the condensation is conducted by using a condenser.

[3] The method for purifying N-(α-alkoxyethyl)formamide according to [1] or [2], in which at least one of the plurality of distillation columns is a packed column.

[4] The method for purifying N-(α-alkoxyethyl)formamide according to any one of [1] to [3], in which a temperature of a column bottom liquid in at least one distillation column among the plurality of distillation columns is 100° C. or less.

[5] The method for purifying N-(α-alkoxyethyl)formamide according to any one of [1] to [4], in which the mixture contains water and an alcohol.

[6] The method for purifying N-(α-alkoxyethyl)formamide according to any one of [1] to [5], in which the condensate contains water and N-(α-alkoxyethyl)formamide.

[7] A method for producing high-purity N-(α-alkoxyethyl)formamide from a mixture containing the N-(α-alkoxyethyl)formamide, water, and an alcohol by using a plurality of distillation columns, in which the plurality of distillation columns are disposed in series, and the method includes:

obtaining an overhead efflux containing an alcohol at a preceding stage and a column bottom liquid at a preceding stage in a distillation column at a preceding stage;

introducing the column bottom liquid at a preceding stage into a distillation column at a subsequent stage;

obtaining an overhead efflux containing water and N-(α-alkoxyethyl)formamide at a subsequent stage and a column bottom liquid containing N-(α-alkoxyethyl)formamide at a subsequent stage in the distillation column at a subsequent stage;

condensing the overhead efflux at a subsequent stage to obtain a condensate; and returning at least a part of the condensate to the distillation column at a preceding stage.

[8] A device for purifying N-(α-alkoxyethyl)formamide, including a plurality of distillation columns for distilling N-(α-alkoxyethyl)formamide-containing liquid, in which the plurality of distillation columns are disposed in series, and the device includes a return section for returning at least a part of a condensate of an overhead efflux of a distillation column at a subsequent stage to a distillation column at a preceding stage.

[9] The device for purifying N-(α-alkoxyethyl)formamide according to [8], including a condenser for condensing the overhead efflux of the distillation column at a subsequent stage.

[10] The device for purifying N-(α-alkoxyethyl)formamide according to [9], in which the condenser is connected to a column top of the distillation column.

[11] The device for purifying N-(α-alkoxyethyl)formamide according to [8] or [9], in which at least one of the plurality of distillation columns is a packed column.

Effect of the Invention

According to the invention, it is possible to provide a method for purifying N-(α-alkoxyethyl)formamide by which N-(α-alkoxyethyl)formamide can be purified at a high recovery rate, a method for producing high-purity N-(α-alkoxyethyl)formamide, and a device for purifying N-(α-alkoxyethyl)formamide.

MODE(S) FOR CARRYING OUT THE INVENTION

The purification method and purification device for N-(α-alkoxyethyl)formamide of the invention are a purification method and a purification device for purifying N-(α-alkoxyethyl)formamide by distilling a solution containing the N-(α-alkoxyethyl)formamide.

The method for producing high-purity N-(α-alkoxyethyl)formamide of the invention is a method for producing high-purity N-(α-alkoxyethyl)formamide by distilling a solution containing the N-(α-alkoxyethyl)formamide.

The N-(α-alkoxyethyl)formamide to be a target of the invention is produced, for example, in the flowing manner.

"Production of N-(α-Alkoxyethyl)Formamide"

N-(α-alkoxyethyl)formamide is obtained by, for example, reacting (hydroxylation reaction) formamide with acetaldehyde in the presence of a basic catalyst to obtain N-(α-hydroxyethyl)formamide and then reacting (alkoxylation reaction) the N-(α-hydroxyethyl)formamide obtained with an alcohol in the presence of an acid catalyst.

<Hydroxylation Reaction>

The molar ratio of formamide to acetaldehyde (formamide:acetaldehyde) is preferably from 1:1 to 1:10 and more preferably from 1:1 to 1:5. It is possible to increase the percent conversion of formamide by setting the molar ratio of acetaldehyde to be excessive.

The reaction temperature in the hydroxylation reaction can be measured by using a thermometer to be usually industrially used such as a thermocouple thermometer. The reaction temperature in the hydroxylation reaction is not particularly limited, and it is usually about from −10° C. to 100° C., but it is preferably from 0° C. to 40° C. from the viewpoint of the hydroxylation reaction yield from formamide to N-(α-hydroxyethyl)formamide and of crystallizing the N-(α-hydroxyethyl)formamide formed. It is possible to increase the hydroxylation reaction yield by crystallizing N-(α-hydroxyethyl)formamide.

The basic catalyst is not particularly limited as long as it is a general basic compound, but it is preferably a weak basic salt composed of a strong base and a weak acid having a pKa value of from 4 to 15, and specific examples thereof may include sodium carbonate, sodium hydrogencarbonate, potassium carbonate, potassium hydrogencarbonate, lithium carbonate, lithium hydrogencarbonate, potassium phosphate, potassium monohydrogen phosphate, and sodium pyrophosphate. Among these, potassium hydrogencarbonate is preferable from the viewpoint of being able to decrease by-products (for example, aldol condensate of acetaldehyde) to be formed at the time of the reaction of formamide with acetaldehyde.

The concentration of the basic catalyst is preferably from 0.3 to 3 moles, more preferably from 0.5 to 1.2 moles, still more preferably from 0.7 to 1 mole, and most preferably from 0.8 to 0.9 mole per 1 kg of formamide.

As the solvent to be used in the hydroxylation reaction, for example, aliphatic hydrocarbons such as hexane, heptane, and cyclohexane; aromatic hydrocarbons such as benzene, toluene, and xylene; and halogenated hydrocarbons such as methylene chloride and chloroform are preferable from the viewpoint of crystallizing N-(α-hydroxyethyl)formamide.

The amount of the solvent used is preferably from 0.2 to 10 times the mass of formamide.

The specific aspect of the hydroxylation reaction is not particularly limited, but it is preferable to spread a mixed liquid of acetaldehyde and a solvent and to drop formamide in which the basic catalyst is dissolved thereon for the hydroxylation reaction. Moreover, a method is generally used in which crystals of N-(α-hydroxyethyl)formamide which is a product are precipitated after the reaction or at the middle stage of the reaction. In addition, an operation of adding a small amount of N-(α-hydroxyethyl)formamide crystals as a seed crystal in the middle of the dropwise addition of formamide in which the basic catalyst is dissolved may be conducted in order to smoothly conduct this crystallization.

By precipitating the crystals of N-(α-hydroxyethyl)formamide, N-(α-hydroxyethyl)formamide can be subjected to the next alkoxylation reaction by simply collecting the crystals by a method such as filtration and further most of the solvent can be separated and recovered. In addition, it is also possible to adopt a method in which the solvent is not separated and recovered from the reaction mixture at this stage but the reaction mixture is subjected to the next alkoxylation reaction as it is.

The reaction mixture contains unreacted formamide and acetaldehyde, an aldol condensate of acetaldehyde which is a by-product of the hydroxylation reaction, the basic catalyst, the solvent, and the like in addition to N-(α-hydroxyethyl)formamide which is a reaction product of formamide with acetaldehyde.

<Alkoxylation Reaction>

In the alkoxylation reaction, the reaction mixture obtained by the hydroxylation reaction described above may be used or N-(α-hydroxyethyl)formamide may be isolated from the reaction mixture and used.

As the alcohol to be used in the alkoxylation reaction, a primary or secondary alcohol is used. Alcohols having from 1 to 8 carbon atoms are preferable and alcohols having from 1 to 4 carbon atoms are more preferable from the viewpoint of reactivity and handling property of N-(α-hydroxyethyl)formamide. Specific examples of the alcohol may include methanol, ethanol, n-propanol, n-butanol, isobutyl alcohol, n-pentanol, n-hexanol, n-heptanol, n-octanol, benzyl alcohol, 2-methoxyethanol, 2-ethoxyethanol, 2-propoxyethanol, 2-butoxyethanol, diethylene glycol monomethyl ether, ethylene glycol, propylene glycol, 1,4-butanediol, and diethylene glycol. Among these, a primary alcohol is preferable and methanol which has a low boiling point as a raw material and provides a product having a low boiling point is particularly preferable.

In order to increase the yield of product, it is preferable to use an excessive amount of alcohol, and specifically, a molar amount to be from 1.1 to 50 times the amount of N-(α-alkoxyethyl)formamide is preferable and a molar amount to be from 2.0 to 30 times the amount of N-(α-alkoxyethyl) formamide is more preferable.

Examples of the acid catalyst to be used in the alkoxylation reaction may include a mineral acid, an organic acid, an ion exchange resin exhibiting weak acidity or strong acidity, and a solid acid catalyst. Among these, a strongly acidic catalyst is preferable, and specific examples thereof may include sulfuric acid, hydrochloric acid, nitric acid, sulfamic acid, methanesulfonic acid, and crosslinked polystyrene sulfonic acid.

As the amount of the acid catalyst used, the total amount of the amount required to neutralize the basic catalyst contained in N-(α-hydroxyethyl)formamide and the amount required to advance the alkoxylation reaction is required. The amount of the acid catalyst used as the total amount is preferably a molar amount to be from 1.01 to 10 times the amount required to neutralize the basic catalyst and more preferably a molar amount to be from 1.1 to 5 times the amount required to neutralize the basic catalyst.

The specific aspect of the alkoxylation reaction is not particularly limited, but for example, the alkoxylation reaction is easily accomplished by adding an acid catalyst to a mixture of N-(α-hydroxyethyl)formamide and an alcohol or bringing these into contact with each other. In addition, a method in which an acid catalyst is dissolved in an alcohol in advance to prepare a catalyst solution and the catalyst solution is then added to N-(α-hydroxyethyl)formamide may be used.

The reaction temperature is preferably from −10° C. to 60° C., more preferably from 0° C. to 40° C., and still more preferably from 5° C. to 30° C. from the viewpoint of the reactivity of the alkoxylation reaction and the stability of N-(α-hydroxyethyl)formamide.

After the completion of the alkoxylation reaction, the acid catalyst is usually neutralized with an alkali compound or it is filtered and separated in a case in which the acid catalyst is in the form of solid such as an ion exchange resin. Incidentally, the neutralization treatment itself is not an essential operation, but it is preferable to conduct the neutralization treatment from the viewpoint of minimizing the decomposition of N-(α-alkoxyethyl)formamide which is a product in the purification and recovery step to be described later since N-(α-alkoxyethyl)formamide is more stable under a neutral condition.

Incidentally, the reaction mixture also contains the basic catalyst used in the hydroxylation reaction in the case of using the reaction mixture obtained by the hydroxylation reaction in the alkoxylation reaction. The basic catalyst reacts with sulfuric acid to form a sulfate such as sodium sulfate or potassium sulfate, for example, in the case of using sulfuric acid as the acid catalyst in the alkoxylation reaction. This sulfate hardly dissolves in the reaction mixture after the completion of the alkoxylation reaction and can be thus separated from the N-(α-alkoxyethyl)formamide by using a filter or the like.

"Purification of N-(α-Alkoxyethyl)Formamide"

The N-(α-alkoxyethyl)formamide thus obtained contains the solvent (hereinafter also referred to as the "reaction solvent") used in the hydroxylation reaction, water formed by the alkoxylation reaction, the excess alcohol which has not been consumed in the alkoxylation reaction, unreacted formamide and acetaldehyde, components having a low boiling point such as an aldol condensate of acetaldehyde which is a by-product of the hydroxylation reaction, soluble salts, and the like as impurities.

Hence, the N-(α-alkoxyethyl)formamide is purified. Hereinafter, an example of the purification method and purification device for N-(α-alkoxyethyl)formamide of the invention will be described with reference to FIG. 1.

<Device for Purifying N-(α-Alkoxyethyl)Formamide>

The device for purifying N-(α-alkoxyethyl)formamide of the invention is a device for purifying N-(α-alkoxyethyl)formamide in which N-(α-alkoxyethyl)formamide-containing liquid is distilled by using a plurality of distillation columns, the plurality of distillation columns are disposed in series in the device, and the device is equipped with a return section for returning at least a part of a condensate of an overhead efflux of a distillation column at a subsequent stage to a distillation column at a preceding stage.

Figure 1:
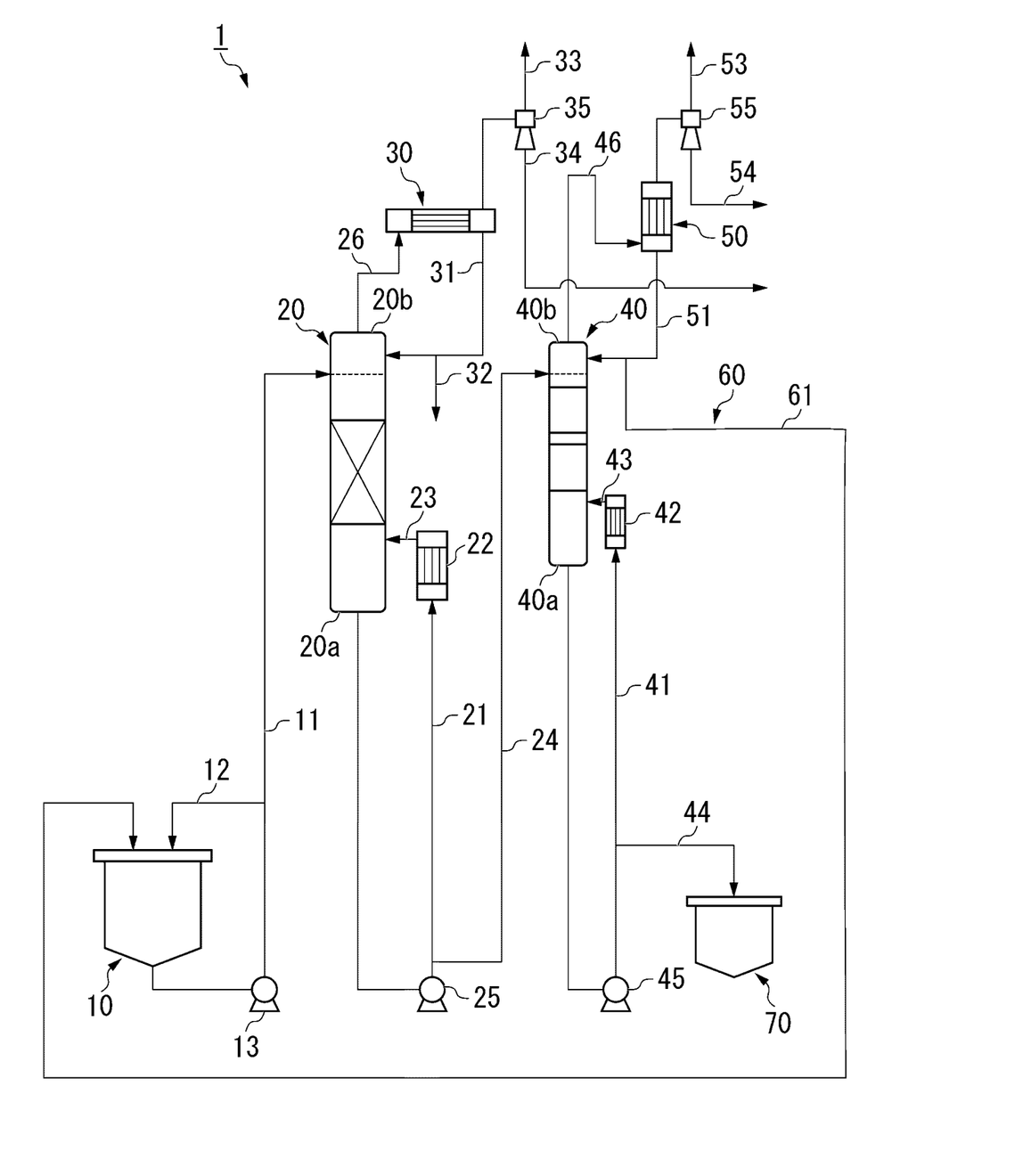
FIG. 1 is a schematic configuration diagram illustrating an example of a device for purifying N-(α-alkoxyethyl)formamide of the invention.

FIG. 1 is a schematic configuration diagram illustrating an example of a device for purifying N-(α-alkoxyethyl)formamide (hereinafter also simply referred to as the "purification device") of the present embodiment. In the present example, a forced circulation reboiler will be described as a preferred device, but the reboiler may be a thermosiphon type or a kettle type and is not limited to the present example.

A purification device 1 of this example is equipped with a storage tank 10 for storing a solution containing N-(α-alkoxyethyl)formamide unpurified, a first distillation column 20 for distilling the solution which contains N-(α-alkoxyethyl)formamide and has been supplied from the storage tank 10, a first condenser 30 connected to the first distillation column 20, a second distillation column 40 provided downstream of the first distillation column 20, a second condenser 50 connected to the second distillation column 40, a return section 60 for returning a part of a condensate of an overhead efflux flowed out from the column top of the second distillation column 40 to the first distillation column 20, and a recovery tank 70 for recovering the N-(α-alkoxyethyl)formamide purified.

Incidentally, in the present embodiment, a solution which contains N-(α-alkoxyethyl)formamide and flows out from a column bottom 20a of the first distillation column 20 is referred to as the "first column bottom liquid (column bottom liquid at a preceding stage)" and the solution which contains N-(α-alkoxyethyl)formamide and flows out from a column bottom 40a of the second distillation column 40 is referred to as the "second column bottom liquid (column bottom liquid at a subsequent stage)".

In addition, the efflux which contains components having a low boiling point and the like and flows out from a column top 20b of the first distillation column 20 is referred to as the "first overhead efflux (overhead efflux at a preceding stage)" and the efflux which contains components having a low boiling point and the like and flows out from a column top 40b of the second distillation column 40 is referred to as the "second overhead efflux (overhead efflux at a subsequent stage)".

In addition, the condensate of the first overhead efflux condensed in the first condenser 30 is referred to as the "first condensate" and the condensate of the second overhead efflux condensed in the second condenser 50 is referred to as the "second condensate".

(Storage Tank)

The storage tank 10 is a tank for storing a solution containing N-(α-alkoxyethyl)formamide unpurified.

The storage tank 10 in this example is equipped with a first supply pipe 11 for supplying a solution containing N-(α-alkoxyethyl)formamide to the first distillation column 20, a first reflow pipe 12 which has branched off from the first supply pipe 11 and is for allowing a part of a solution containing N-(α-alkoxyethyl)formamide to reflow into the storage tank 10, and a first supply pump 13 provided to the first supply pipe 11.

(First Distillation Column)

The first distillation column 20 is a distillation column for distilling a solution which contains N-(α-alkoxyethyl)formamide and has been supplied from the storage tank 10 and mainly separates alcohols having a low boiling point.

The first distillation column 20 in this example is equipped with a first column bottom outflow pipe 21 for allowing the first column bottom liquid to flow out from the column bottom 20a of the first distillation column 20, a first reboiler 22 for heating a part of the first column bottom liquid sent through the first column bottom outflow pipe 21, a second reflow pipe 23 for allowing the first column bottom liquid heated by the first reboiler 22 to reflow into the first distillation column 20, a second supply pipe 24 which has branched off from the first column bottom outflow pipe 21 and is for supplying the remainder of the first column bottom liquid sent through the first column bottom outflow pipe 21 to the second distillation column 40, a second supply pump 25 provided to the first column bottom outflow pipe 21, and a first overhead outflow pipe 26 for allowing the first overhead effluent vaporized to flow out from the column top 20b of the first distillation column 20.

The first distillation column 20 is not particularly limited as long as it can purify a solution containing N-(α-alkoxyethyl)formamide by distillation, but examples thereof may include a packed column and a plate column. Among these, a packed column is preferable from the viewpoint of low pressure loss, high treatment capacity by distillation, simple structure, and relatively low cost.

It is preferable that the first distillation column 20 is packed with a structured packing in a case in which the first distillation column 20 is a packed column.

The flow rate of the solution which contains N-(α-alkoxyethyl)formamide and is supplied is larger (the amount treated by distillation is larger) in the first distillation column 20 than in the second distillation column 40, and thus the pressure loss in the first distillation column 20 tends to be higher than the pressure loss in the second distillation column 40. A structured packing has a lower pressure loss than a random packing, and it is thus possible to diminish the pressure loss in the column by packing the first distillation column 20 with a structured packing. In addition, a structured packing has a high treatment capacity by distillation, and it is thus possible to decrease the size of the column.

The structured packing is not particularly limited as long as it can be used for distillation, but examples thereof may include those obtained by bending and processing a metal or plastic thin plate and those obtained by bending and processing a metal mesh.

Commercially available products can be used as the structured packing, and examples thereof may include "Mellapack", "Mellapack Plus", "Gauze packing", and "Mellagrid" manufactured by Sulzer Chemtech Ltd. and "SFLOW" and "MELLAPACK 250Y" manufactured by Sumitomo Heavy Industries, Ltd.

(First Condenser)

The first condenser 30 is a condenser for condensing the first overhead effluent which has been vaporized and supplied from the first distillation column 20.

The first condenser 30 in this example is equipped with a first reflux pipe 31 for returning a part of the first condensate to the first distillation column 20 and refluxing it, a first discharge pipe 32 which has branched off from the first reflux pipe 31 and is for discharging the remainder of the first condensate to the outside of the system, a second discharge pipe 33 for discharging the first overhead effluent which has not been condensed and is in the form of vapor from the first condenser 30 to the outside of the system, a third discharge pipe 34 which has branched off from the second discharge pipe 33 and is for discharging the first overhead effluent which has been cooled and liquefied in the second discharge pipe 33 to the outside of the system, and a first vacuum pump 35 provided to the second discharge pipe 33.

The first overhead effluent mainly contains the vaporized reaction solvent, alcohols, water, and the like.

(Second Distillation Column)

The second distillation column 40 is a distillation column for distilling the first column bottom liquid supplied from the first distillation column 20 and mainly separates water.

The second distillation column 40 in this example is equipped with a second column bottom outflow pipe 41 for allowing the second column bottom liquid to flow out from the column bottom 40a of the second distillation column 40, a second reboiler 42 for heating a part of the second column bottom liquid sent through the second column bottom outflow pipe 41, a third reflow pipe 43 for allowing the second column bottom liquid heated by the second reboiler 42 to reflow into the second distillation column 40, a third supply pipe 44 which has branched off from the second column bottom outflow pipe 41 and is for supplying the remainder of the second column bottom liquid sent through the second column bottom outflow pipe 41 to the recovery tank 70, a third supply pump 45 provided to the second column bottom outflow pipe 41, and a second overhead outflow pipe 46 for allowing the second overhead effluent vaporized to flow out from the column top 40b of the second distillation column 40.

The second distillation column 40 is not particularly limited as long as it can purify the first column bottom liquid by distillation, but examples thereof may include a packed column and a plate column. Among these, a packed column is preferable from the viewpoint of low cost and low pressure loss.

The second distillation column 40 may be packed with a random packing or a structured packing in a case in which the second distillation column 40 is a packed column. However, the flow rate of the solution which contains N-(α-alkoxyethyl)formamide and is supplied is smaller (the amount treated by distillation is smaller) in the second distillation column 40 than in the first distillation column 20 and thus the pressure loss in the second distillation column 40 tends to be lower than the pressure loss in the first distillation column 20 when the two columns have the same column diameter. For this reason, a random packing is sufficient as a packing to be packed in the second distillation column 40.

The random packing is not particularly limited as long as it can be used for distillation, but examples thereof may include those obtained by processing a metal or plastic thin plate into various shapes such as a cylindrical shape and a saddle shape of a horse.

Commercially available products can be used as the random packing, and examples thereof may include "Nutter Rings", "I-Rings", "C-Rings", "P-Rings", and "R-Rings" manufactured by Sulzer Chemtech Ltd and "IMTP #25" manufactured by IWAOKA JIKI KOGYO CO., LTD.

As the structured packing, the same ones as those of the first distillation column 20 are exemplified.

(Second Condenser)

The second condenser 50 is a condenser for condensing the second overhead efflux which has been vaporized and supplied from the second distillation column 40.

The second condenser 50 in this example is equipped with a second reflux pipe 51 for returning a part of the second condensate to the second distillation column 40 and refluxing it, a fourth discharge pipe 53 for discharging the second overhead efflux which has not been condensed and is in the form of vapor from the second condenser 50 to the outside of the system, a fifth discharge pipe 54 which has branched off from the fourth discharge pipe 53 and is for discharging the second overhead efflux which has been cooled and liquefied in the fourth discharge pipe 53 to the outside of the system, and a second vacuum pump 55 provided to the fourth discharge pipe 53.

The second overhead efflux mainly contains vaporized water, aldol condensates, and the like. The second overhead efflux also contains the reaction solvent and alcohols which have not been able to be removed in the first distillation column 20. The second overhead efflux further contains a part of N-(α-alkoxyethyl)formamide vaporized.

(Return Section)

The return section 60 is a measure for returning a part of the second condensate to the first distillation column 20.

The return section 60 in this example is equipped with a return pipe 61 which has branched off from the second reflux pipe 51 and is connected to the storage tank 10.

The second condensate mainly contains N-(α-alkoxyethyl)formamide, water, and the like that have been condensed in the second condenser 50.

(Recovery Tank)

The recovery tank 70 is a tank for recovering N-(α-alkoxyethyl)formamide (second column bottom liquid) after purification.

(Effect)

The purification device 1 of the present embodiment is equipped with the first distillation column 20 and the second distillation column 40 which are disposed in series and the return section 60 for returning a part of the condensate (second condensate) of the second overhead efflux flowed out from the column top 40b of the second distillation column 40 (distillation column at the subsequent stage) to the first distillation column 20 (distillation column at the preceding stage). The second condensate contains N-(α-alkoxyethyl)formamide. Conventionally, the second condensate which has not been refluxed to the second distillation column 40 has been discharged to the outside of the system and was discarded.

However, in the purification device 1 of the present embodiment, the second condensate containing N-(α-alkoxyethyl)formamide is returned to the first distillation column 20 and thus the N-(α-alkoxyethyl)formamide which has been conventionally discarded can be supplied to the purification cycle again.

Consequently, according to the purification device 1 of the present embodiment, it is possible to purify N-(α-alkoxyethyl)formamide at a high recovery rate.

Incidentally, the term "recovery rate" in the invention refers to the proportion of the N-(α-alkoxyethyl)formamide which has passed through all the distillation columns and is recovered to the N-(α-alkoxyethyl)formamide before purification.

<Method for Purifying N-(α-Alkoxyethyl)Formamide>

The method for purifying N-(α-alkoxyethyl)formamide of the invention is a method for purifying N-(α-alkoxyethyl) formamide from a mixture containing the N-(α-alkoxyethyl) formamide by using a plurality of distillation columns, the plurality of distillation columns are disposed in series in the purification method, and the method includes: condensing an overhead efflux of a distillation column at a subsequent stage to obtain a condensate; and returning at least a part of the condensate to a distillation column at a preceding stage.

The method for purifying N-(α-alkoxyethyl)formamide (hereinafter also simply referred to as the "purification method") by using the purification device 1 includes a first distillation step, a second distillation step, and a return step which are described below.

(First Distillation Step)

First, the first supply pump 13 is run and a solution containing N-(α-alkoxyethyl)formamide unpurified is supplied from the storage tank 10 to the first distillation column 20 through the first supply pipe 11. At this time, a part of the solution containing N-(α-alkoxyethyl)formamide flows into the storage tank 10 through the first reflow pipe 12. The liquid can be stably supplied to the first distillation column 20 as the first reflow pipe 12 is equipped.

The solution which contains N-(α-alkoxyethyl)formamide and has been supplied to the first distillation column 20 flows down to the column bottom 20a of the first distillation column 20 while coming into contact with vapor. The solution which contains N-(α-alkoxyethyl)formamide and has reached the column bottom 20a is sent as the first column bottom liquid from the column bottom 20a to the first reboiler 22 by the second supply pump 25 to be heated and circulated and a part thereof is withdrawn from the second supply pipe 24. In the first distillation column 20, the downward flow of the solution containing N-(α-alkoxyethyl)formamide and the vapor of the column bottom liquid ascended come into contact with each other and the mass transfer and heat transfer between gas and liquid are thus repeated. As a result, components which have a low boiling point and are contained in the solution containing N-(α-alkoxyethyl)formamide and the N-(α-alkoxyethyl)formamide having a high boiling point are separated from each other.

Subsequently, the first overhead efflux which is in the form of vapor and has reached the column top 20b of the first distillation column 20 is introduced into the first condenser 30 through the first overhead outflow pipe 26, cooled, condensed, and liquefied. The overhead liquid passes through the first discharge pipe 32 and is discharged to the outside of the system.

In addition, the first overhead efflux which is in the form of vapor and has not been condensed in the first condenser 30 is discharged to the outside of the system through the first vacuum pump 35 or an ejector (not illustrated).

The first overhead efflux mainly contains the vaporized reaction solvent, alcohols, water, and the like.

Meanwhile, the first column bottom liquid flowing out from the column bottom 20a of the first distillation column 20 contains N-(α-alkoxyethyl)formamide separated from the components having a low boiling point at a high concentration. As described above, a part of this first column bottom liquid is vaporized by being heated by the first reboiler 22 and then flows into the first distillation column 20 again. The remainder of first column bottom liquid withdrawn is supplied to the second distillation column 40 through the second supply pipe 24.

In the first distillation step, the temperature of the first column bottom liquid is preferably 100° C. or less, more preferably from 70° C. to 100° C., and still more preferably from 80° C. to 86° C. The amount of N-(α-alkoxyethyl) formamide decomposed increases when the temperature of the first column bottom liquid exceeds 100° C. On the other hand, the components which have a low boiling point and are to be separated decrease and the purity of N-(α-alkoxyethyl)formamide to be sent to the second distillation column decreases when the temperature of the first column bottom liquid is less than 70° C. It is required to lower the pressure of the distillation column in order to lower the column bottom temperature while maintaining the purity of N-(α-alkoxyethyl)formamide.

In the first distillation step, the pressure at the column top 20b of the first distillation column 20 (first overhead pressure) is preferably from 4 to 20 kPa and more preferably from 6 to 10 kPa. Components which have a low boiling point and cannot be condensed in the condenser at the column top increase and, as a result, the loss of components having a low boiling point increases when the first overhead pressure is less than 4 kPa. On the other hand, the temperature at the column bottom increases and the loss of N-(α-alkoxyethyl)formamide by decomposition increases when the first overhead pressure exceeds 20 kPa.

The first overhead pressure is usually controlled by the control valve attached to the line of a vacuum instrument such as a vacuum pump or an ejector, and the column bottom temperature is also controlled in accordance with the overhead pressure at that time.

(Second Distillation Step)

The first column bottom liquid supplied to the second distillation column 40 flows down to the column bottom 40a of the second distillation column 40 while coming into contact with vapor and sent to the second reboiler 42 by the third supply pump 45 to be heated and circulated and a part thereof is withdrawn from the third supply pipe 44. The gas and liquid come into contact with each other in association with the downward flow of the first column bottom liquid in the form of liquid and the ascent of the second column bottom liquid in the form of vapor in the second distillation column 40 and the mass transfer and heat transfer between gas and liquid are thus repeated. As a result, components having a low boiling point are withdrawn from the column top and the components which have a low boiling point and are contained in the solution containing N-(α-alkoxyethyl)formamide and the N-(α-alkoxyethyl)formamide having a high boiling point are further separated from each other.

The second overhead efflux which is in the form of vapor and has flowed out from the column top 40b of the second distillation column 40 passes through the second overhead outflow pipe 46 and is condensed and liquefied in the second condenser 50. Subsequently, a part of the second condensate liquefied in the second condenser 50 is returned to the second distillation column 40 through the second reflux pipe 51, refluxed, and allowed to flow down in the second distillation column 40.

In addition, the second overhead efflux which is in the form of vapor and has not been condensed in the second condenser 50 is sucked into the second vacuum pump 55. For this reason, it is preferable to completely condense the vapor phase components in the second condenser 50.

The second overhead efflux mainly contains vaporized water, aldol condensates, and the like. The second overhead efflux also contains the reaction solvent and alcohols which have not been able to be removed in the first distillation column 20. The second overhead efflux further contains a part of N-(α-alkoxyethyl)formamide vaporized since the pressure at the column top 40b of the second distillation column 40 (second overhead pressure) is lower than the first overhead pressure.

Meanwhile, the second column bottom liquid flowing out from the column bottom 40a of the second distillation column 40 contains N-(α-alkoxyethyl)formamide concentrated at a high concentration. This second column bottom liquid is withdrawn into the recovery tank 70, but a part thereof is ascended by the second reboiler 42 as described above.

In the second distillation step, the temperature of the second column bottom liquid is preferably 100° C. or less, more preferably from 70° C. to 100° C., and still more preferably from 80° C. to 86° C. The amount of N-(α-alkoxyethyl)formamide decomposed increases when the temperature of the second column bottom liquid exceeds 100° C. On the other hand, the components which have a low boiling point and are to be separated decrease and the purity of N-(α-alkoxyethyl)formamide decreases when the temperature of the second column bottom liquid is less than 70° C. It is required to lower the pressure of the distillation column in order to lower the column bottom temperature while maintaining the purity of N-(α-alkoxyethyl)formamide.

In the second distillation step, the second overhead pressure is preferably from 0.1 to 4 kPa and more preferably from 1 to 2 kPa. When the second overhead pressure is less than 0.1 kPa, the N-(α-alkoxyethyl)formamide which ascends from the column increases and the loss of N-(α-alkoxyethyl)formamide increases although the column bottom temperature decreases, and the components which cannot be condensed in the second condenser 50 but are lost through the pump increase. On the other hand, the column bottom temperature increases and the loss of N-(α-alkoxyethyl)formamide by decomposition increases when the second overhead pressure exceeds 4 kPa.

The second overhead pressure is usually controlled by the control valve attached to the line of a vacuum instrument such as a vacuum pump or an ejector, and the column bottom temperature is also controlled in accordance with the overhead pressure at that time.

(Return Step)

The remainder of the second condensate which has not been returned to the second distillation column 40 is returned to the storage tank 10 through the return pipe 61 of the return section 60. The second condensate returned to the storage tank 10 is supplied to the first distillation column 20 together with the solution which contains N-(α-alkoxyethyl)formamide and has been stored in the storage tank 10, distilled again, and purified.

The second condensate mainly contains N-(α-alkoxyethyl)formamide, water, and the like that have been condensed in the second condenser 50.

(Effect)

In the purification method of the present embodiment, a part of the condensate (second condensate) of the second overhead efflux flowed out from the column top 40b of the second distillation column 40 (distillation column at the subsequent stage) is returned to the first distillation column 20 (distillation column at the preceding stage) when purifying N-(α-alkoxyethyl)formamide by using the first distillation column 20 and the second distillation column 40 which are disposed in series. The second condensate contains N-(α-alkoxyethyl)formamide.

According to the purification method of the present embodiment, the second condensate containing N-(α-alkoxyethyl)formamide is returned to the first distillation column 20 in this manner and thus N-(α-alkoxyethyl)formamide which has been conventionally discarded can be supplied to the purification cycle again. Consequently, according to the purification method of the present embodiment, it is possible to purify N-(α-alkoxyethyl)formamide at a high recovery rate.

<Method for Producing High-Purity N-(α-Alkoxyethyl) Formamide>

The method for producing high-purity N-(α-alkoxyethyl)formamide of the invention (hereinafter also simply referred to as the "production method" is a method for producing high-purity N-(α-alkoxyethyl)formamide from a mixture containing the N-(α-alkoxyethyl)formamide, water, and an alcohol by using a plurality of distillation columns, the plurality of distillation columns are disposed in series in the method, and the method includes: obtaining (step 1) an overhead efflux containing an alcohol at a preceding stage and a column bottom liquid at a preceding stage in a distillation column at a preceding stage; introducing (step 2) the column bottom liquid at a preceding stage into a distillation column at a subsequent stage; obtaining (step 3) an overhead efflux containing water and N-(α-alkoxyethyl)formamide at a subsequent stage and a column bottom liquid containing N-(α-alkoxyethyl)formamide at a subsequent stage in the distillation column at a subsequent stage; condensing (step 4) the overhead efflux at a subsequent stage to obtain a condensate; and returning (step 5) at least a part of the condensate to the distillation column at a preceding stage.

Incidentally, high-purity N-(α-alkoxyethyl)formamide refers to N-(α-alkoxyethyl)formamide in which the content of impurities is less than 15% by mass with respect to the total mass of N-(α-alkoxyethyl)formamide containing impurities.

Examples of the impurities may include the reaction solvent used in the hydroxylation reaction, water formed by the alkoxylation reaction, the excess alcohol which has not been consumed in the alkoxylation reaction, unreacted formamide and acetaldehyde, components having a low boiling point such as an aldol condensate of acetaldehyde which is a by-product of the hydroxylation reaction, and soluble salts.

In the production method of the invention, it is preferable to use the purification device 1.

(Step (1))

First, the first supply pump 13 is run and a solution containing N-(α-alkoxyethyl)formamide unpurified is supplied from the storage tank 10 to the first distillation column 20 through the first supply pipe 11. At this time, a part of the solution containing N-(α-alkoxyethyl)formamide flows into the storage tank 10 through the first reflow pipe 12. The liquid can be stably supplied to the first distillation column 20 as the first reflow pipe 12 is equipped.

The solution containing N-(α-alkoxyethyl)formamide supplied to the first distillation column 20 flows down to the column bottom 20a of the first distillation column 20 while coming into contact with vapor. The solution which contains N-(α-alkoxyethyl)formamide and has reached the column bottom 20a is sent as the first column bottom liquid from the column bottom 20a to the first reboiler 22 by the second supply pump 25 to be heated and circulated and a part thereof is withdrawn from the second supply pipe 24. In the first distillation column 20, the downward flow of the solution containing N-(α-alkoxyethyl)formamide and the vapor of the column bottom liquid ascended come into contact with each other and the mass transfer and heat transfer between gas and liquid are thus repeated. As a result, components which have a low boiling point and are contained in the solution containing N-(α-alkoxyethyl)formamide and the N-(α-alkoxyethyl)formamide having a high boiling point are separated from each other.

Subsequently, the first overhead efflux which is in the form of vapor and has reached the column top 20b of the first distillation column 20 is introduced into the first condenser 30 through the first overhead outflow pipe 26, cooled, condensed, and liquefied. The overhead liquid passes through the first discharge pipe 32 and is discharged to the outside of the system.

In addition, the first overhead efflux which is in the form of vapor and has not been condensed in the first condenser 30 is discharged to the outside of the system through the first vacuum pump 35 or an ejector (not illustrated).

The first overhead efflux mainly contains the vaporized reaction solvent, alcohols, water, and the like.

Meanwhile, the first column bottom liquid flowing out from the column bottom 20a of the first distillation column 20 contains N-(α-alkoxyethyl)formamide separated from components having a low boiling point at a high concentration. As described above, a part of this first column bottom liquid is vaporized by being heated by the first reboiler 22 and then flows into the first distillation column 20 again. The remainder of first column bottom liquid withdrawn is supplied to the second distillation column 40 through the second supply pipe 24.

The temperature of the first column bottom liquid is preferably 100° C. or less, more preferably from 70° C. to 100° C., and still more preferably from 80° C. to 86° C. The amount of N-(α-alkoxyethyl)formamide decomposed increases when the temperature of the first column bottom liquid exceeds 100° C. On the other hand, the components which have a low boiling point and are to be separated decrease and the purity of N-(α-alkoxyethyl)formamide to be sent to the second distillation column decreases when the temperature of the first column bottom liquid is less than 70° C. It is required to lower the pressure of the distillation column in order to lower the column bottom temperature while maintaining the purity of N-(α-alkoxyethyl)formamide.

The pressure at the column top 20b of the first distillation column 20 (first overhead pressure) is preferably from 4 to 20 kPa and more preferably from 6 to 10 kPa. Components which have a low boiling point and cannot be condensed in the condenser at the column top increase and, as a result, the loss of components having a low boiling point increases when the first overhead pressure is less than 4 kPa. On the other hand, the column bottom temperature increases and the loss of N-(α-alkoxyethyl)formamide by decomposition increases when the first overhead pressure exceeds 20 kPa.

The first overhead pressure is usually controlled by the control valve attached to the line of a vacuum instrument such as a vacuum pump or an ejector, and the column bottom temperature is also controlled in accordance with the overhead pressure at that time.

(Step (2))

The first column bottom liquid is supplied to the second distillation column 40 through the second supply pipe 24.

(Step (3))

The first column bottom liquid supplied to the second distillation column 40 flows down to the column bottom 40a of the second distillation column 40 while coming into contact with vapor and sent to the second reboiler 42 by the third supply pump 45 to be heated and circulated and a part thereof is withdrawn from the third supply pipe 44. The gas and liquid come into contact with each other in association with the downward flow of the first column bottom liquid in the form of liquid and the ascent of the second column bottom liquid in the form of vapor in the second distillation column 40 and the mass transfer and heat transfer between gas and liquid are thus repeated. As a result, components having a low boiling point are withdrawn as the second overhead efflux from the column top and the components which have a low boiling point and are contained in the solution containing N-(α-alkoxyethyl)formamide and the N-(α-alkoxyethyl)formamide having a high boiling point are further separated from each other.

(Step (4))

The second overhead efflux which is in the form of vapor and has flowed out from the column top 40*b* of the second distillation column 40 passes through the second overhead outflow pipe 46 and is condensed and liquefied in the second condenser 50. Subsequently, a part of the second condensate liquefied in the second condenser 50 is returned to the second distillation column 40 through the second reflux pipe 51, refluxed, and allowed to flow down in the second distillation column 40.

In addition, the second overhead efflux which is in the form of vapor and has not been condensed in the second condenser 50 is sucked into the second vacuum pump 55. For this reason, it is preferable to completely condense the vapor phase components in the second condenser 50.

The second overhead efflux mainly contains vaporized water, aldol condensates, and the like. The second overhead efflux also contains the reaction solvent and alcohols which have not been able to be removed in the first distillation column 20. The second overhead efflux further contains a part of N-(α-alkoxyethyl)formamide vaporized since the pressure at the column top 40*b* of the second distillation column 40 (second overhead pressure) is lower than the first overhead pressure.

Meanwhile, the second column bottom liquid flowing out from the column bottom 40*a* of the second distillation column 40 contains N-(α-alkoxyethyl)formamide concentrated at a high concentration. This second column bottom liquid is withdrawn into the recovery tank 70, but a part thereof is ascended by the second reboiler 42 as described above.

The temperature of the second column bottom liquid is preferably 100° C. or less, more preferably from 70° C. to 100° C., and still more preferably from 80° C. to 86° C. The amount of N-(α-alkoxyethyl)formamide decomposed increases when the temperature of the second column bottom liquid exceeds 100° C. On the other hand, the components which have a low boiling point and are to be separated decrease and the purity of N-(α-alkoxyethyl)formamide decreases when the temperature of the second column bottom liquid is less than 70° C. It is required to lower the pressure of the distillation column in order to lower the column bottom temperature while maintaining the purity of N-(α-alkoxyethyl)formamide.

The second overhead pressure is preferably from 0.1 to 4 kPa and more preferably from 1 to 2 kPa. When the second overhead pressure is less than 0.1 kPa, the N-(α-alkoxyethyl)formamide which ascends from the column increases and the loss of N-(α-alkoxyethyl)formamide increases although the column bottom temperature decreases, and the components which cannot be condensed in the second condenser 50 but are lost through the pump increase. On the other hand, the column bottom temperature increases and the loss of N-(α-alkoxyethyl)formamide by decomposition increases when the second overhead pressure exceeds 4 kPa.

The second overhead pressure is usually controlled by the control valve attached to the line of a vacuum instrument such as a vacuum pump or an ejector, and the column bottom temperature is also controlled in accordance with the overhead pressure at that time.

(Step (5))

The remainder of the second condensate which has not been returned to the second distillation column 40 is returned to the storage tank 10 through the return pipe 61 of the return section 60. The second condensate returned to the storage tank 10 is supplied to the first distillation column 20 together with the solution which contains N-(α-alkoxyethyl)formamide and has been stored in the storage tank 10, distilled again, and purified.

The second condensate mainly contains N-(α-alkoxyethyl)formamide, water, and the like that have been condensed in the second condenser 50.

(Effect)

In the production method of the present embodiment, a part of the condensate (second condensate) of the second overhead efflux flowed out from the column top 40*b* of the second distillation column 40 (distillation column at the subsequent stage) is returned to the first distillation column 20 (distillation column at the preceding stage) when producing high-purity N-(α-alkoxyethyl)formamide by using the first distillation column 20 and the second distillation column 40 which are disposed in series. The second condensate contains N-(α-alkoxyethyl)formamide.

According to the production method of the present embodiment, the second condensate containing N-(α-alkoxyethyl)formamide is returned to the first distillation column 20 in this manner and thus N-(α-alkoxyethyl)formamide which has been conventionally discarded can be supplied to the purification cycle again. Consequently, according to the production method of the present embodiment, it is possible to produce high-purity N-(α-alkoxyethyl)formamide at a high recovery rate.

OTHER EMBODIMENTS

The purification device, purification method, and production method of the present embodiment are not limited to those described above. For example, in the purification device 1 illustrated in FIG. 1 and the purification method and production method using the purification device 1, the second condensate is returned to the first distillation column 20 through the storage tank 10 by the return section 60, but the second condensate may be directly returned to the first distillation column 20 by the return section 60. In other words, the return pipe 61 of the return section 60 may be connected to the first distillation column 20.

In addition, the storage tank 10 may not be equipped with the first reflow pipe 12.

In addition, the purification device 1 illustrated in FIG. 1 is equipped with two distillation columns, but the number of distillation columns may be three or more. In the case of purifying N-(α-alkoxyethyl)formamide by using three or more distillation columns disposed in series, it is preferable to return a part of the condensate of the overhead efflux flowed out from the column top of at least the distillation column at the most downstream among the three or more distillation columns to a distillation column at the upstream (preceding stage) of the distillation column at the most downstream. For example, in the case of purifying N-(α-alkoxyethyl)formamide by using three or more distillation columns disposed in series, it is preferable to return a part of the condensate of the overhead efflux flowed out from the column top of the third distillation column to at least either of the first distillation column or the second distillation column. At that time, a part of the condensate of the overhead efflux flowed out from the column top of the second distillation column may be returned to the first distillation column.

EXAMPLES

Hereinafter, the invention will be more specifically described with reference to Examples, but the invention is not limited thereto. Incidentally, "%" represents "% by mass" unless otherwise stated.

Example 1

By using the purification device 1 illustrated in FIG. 1, N-(α-methoxyethyl)formamide was purified in the following manner.

<Production of N-(α-Methoxyethyl)Formamide>

A formamide solution of potassium hydrogencarbonate was prepared by dissolving 1.69 kg of potassium hydrogencarbonate in 95.2 kg of formamide.

Separately, 384 kg of toluene for industrial use was charged into a hydroxylation reaction tank which was made of glass lining and equipped with a stirrer and a temperature controller, the hydroxylation reaction tank was purged with nitrogen gas, 107 kg of acetaldehyde was then added to the toluene, and the temperature was adjusted to 20° C.

Subsequently, 20% of the formamide solution of potassium hydrogencarbonate was added to the toluene solution of acetaldehyde in the hydroxylation reaction tank over 30 minutes. The mixture was subjected to aging for 1 hour, then the remaining amount of the formamide solution of potassium hydrogencarbonate was further added thereto over 2.5 hours, and the mixture was further subjected to aging (hydroxylation reaction) for 1 hour to obtain a reaction slurry.

The reaction slurry obtained was transferred to the alkoxylation reaction tank which was made of glass lining and equipped with a stirrer and a temperature controller and filtered to separate most of toluene of a solvent. To the solid component (reaction mixture) filtered, 2.05 kg of 98% sulfuric acid and 203.1 kg of methanol were added, and the reaction (alkoxylation reaction) thereof was conducted at 20° C. for 1 hour.

Subsequently, a 25% aqueous solution of sodium hydroxide was added to the resultant mixture until the pH reached 7 to neutralize the acid catalyst (sulfuric acid). Thereafter, potassium sulfate (inorganic salt) which was a reaction product of potassium hydrogencarbonate with sulfuric acid was separated from the mixture by using a metal filter type pressurized filter (Model AAF-5734 manufactured by Fuji Filter Manufacturing Co., Ltd) made of SUS 304.

The filtrate obtained by this solid-liquid separation was analyzed by liquid chromatography under the following conditions, and as a result, the filtrate contained N-(α-methoxyethyl)formamide at 45.5%, formamide at 0.3%, N-(α-hydroxyethyl)formamide at 0.8%, and water at 9.3%.

(Conditions for Liquid Chromatography Analysis)
Column: MCI-GEL-ODS 1HU (4.6 mm φ×250 mm).
Flow rate: 1 mL/min.
Eluent: 0.01 M $NaH_2PO_3 \cdot 2H_2O$ aqueous solution.
Sample injection volume: 20 μL of sample diluted with eluent by 1000 times.

<Purification of N-(α-Methoxyethyl)Formamide>

The first distillation column 20 illustrated in FIG. 1 was packed with a structured packing ("MELLAPACK 250Y" manufactured by Sumitomo Heavy Industries, Ltd.), and the second distillation column 40 was packed with a random packing ("IMTP #25" manufactured by IWAOKA JIKI KOGYO CO., LTD.).

The filtrate (solution containing N-(α-methoxyethyl)formamide unpurified) which contained N-(α-methoxyethyl)formamide at 45.5% and was thus obtained was stored in the storage tank 10.

The first supply pump 13 was run and the solution containing N-(α-methoxyethyl)formamide unpurified was supplied from the storage tank 10 to the first distillation column 20 at a flow rate of 58 kg/hr.

Thereafter, the solution containing N-(α-methoxyethyl)formamide was allowed to flow down and was sent as the first column bottom liquid from the column bottom 20a of the first distillation column 20 to the first reboiler 22. The vapor of the first column bottom liquid was generated in the first reboiler 22 and this vapor was reintroduced into the first distillation column 20. In this manner, the solution containing N-(α-methoxyethyl)formamide and the first column bottom liquid in the form of vapor were brought into contact with each other and the mass transfer and heat transfer between gas and liquid were repeated in the first distillation column 20 to separate components having a low boiling point and N-(α-methoxyethyl)formamide from each other and to concentrate the components having a low boiling point in the column top 20b and N-(α-methoxyethyl)formamide in the column bottom 20a.

Subsequently, the first overhead efflux which was in the form of vapor and had flowed out through the first overhead outflow pipe 26 was introduced into and condensed in the first condenser 30 using water at 4° C. as a refrigerant. Subsequently, a part of the condensate (first condensate) of the first overhead efflux was returned to the first distillation column 20, refluxed, and allowed to flow down in the first distillation column 20, and the remainder of the first condensate was discharged to the outside of the system through the first discharge pipe 32.

In addition, the first overhead efflux which was in the form of vapor and had not been condensed in the first condenser 30 was discharged to the outside of the system through the second discharge pipe 33 by the first vacuum pump 35. At that time, the first overhead efflux which had been cooled and liquefied in the second discharge pipe 33 was discharged to the outside of the system through the third discharge pipe 34.

Meanwhile, a part of the first column bottom liquid discharged from the column bottom 20a of the first distillation column 20 was vaporized in the first reboiler 22 as described above and reintroduced into the first distillation column 20 and the remainder of the first column bottom liquid was supplied to the second distillation column 40 through the second supply pipe 24 at a flow rate of 29 kg/hr.

The pressure at the column top of the first distillation column 20 (first overhead pressure) was from 8 to 10 kPa, and the temperature of the first column bottom liquid flowing out from the column bottom 20a of the first distillation column 20 was from 80° C. to 86° C.

The first column bottom liquid supplied to the second distillation column 40 was allowed to flow down and was sent as the second column bottom liquid from the column bottom 40a of the second distillation column 40 to the second reboiler 42. The vapor of the second column bottom liquid was generated in the second reboiler 42, and this vapor was reintroduced into the second distillation column 40. In this manner, the first column bottom liquid in the form of liquid and the second column bottom liquid in the form of vapor were brought into contact with each other and the mass transfer and heat transfer between gas and liquid were repeated in the second distillation column 40 to further separate components having a low boiling point and N-(α-methoxyethyl)formamide from each other and to concentrate the components having a low boiling point in the column top 40b and N-(α-methoxyethyl)formamide in the column bottom 40a.

Subsequently, the second overhead efflux which was in the form of vapor and had flowed out through the second overhead outflow pipe 46 was introduced into and condensed in the second condenser 50 using water at 4° C. as a refrigerant. Subsequently, a part of the condensate (second condensate) of the second overhead efflux was returned to the second distillation column 40, refluxed, and allowed to flow down in the second distillation column 40.

In addition, the second overhead efflux which was in the form of vapor and had not been condensed in the second condenser 50 was discharged to the outside of the system through the fourth discharge pipe 53 by the second vacuum pump 55. At that time, the second overhead efflux which had been cooled and liquefied in the fourth discharge pipe 53 was discharged to the outside of the system through the fifth discharge pipe 54.

Meanwhile, a part of the second column bottom liquid discharged from the column bottom 40a of the second distillation column 40 was vaporized in the second reboiler 42 as described above and reintroduced into the second distillation column 40 and the remainder of the second column bottom liquid was recovered into the recovery tank 70 through the third supply pipe 44 at a flow rate of 28 kg/hr.

The pressure at the column top of the second distillation column 40 (second overhead pressure) was from 1 to 1.6 kPa, and the temperature of the second column bottom liquid flowing out from the column bottom 40a of the second distillation column 40 was from 78° C. to 84° C.

In addition, the remainder of the second condensate which had not been returned to the second distillation column 40 was returned to the storage tank 10 through the return pipe 61 of the return section 60 at a flow rate of 1 kg/hr. Thereafter, the second condensate returned to the storage tank 10 was supplied to the first distillation column 20 together with the solution which contained N-(α-methoxyethyl)formamide and had been stored in the storage tank 10, distilled again, and purified.

The second column bottom liquid recovered in the recovery tank 70 was analyzed by liquid chromatography under the above conditions, and as a result, the liquid contained N-(α-methoxyethyl)formamide at 95.0%, formamide at 0.62%, N-(α-hydroxyethyl)formamide at 0.17%, and water at 0.35%.

From the above results, the proportion (recovery rate) of N-(α-methoxyethyl)formamide which passed through the first distillation column 20 and the second distillation column 40 and was then recovered was 99.9% in a case in which N-(α-methoxyethyl)formamide was distilled while returning the second condensate to the first distillation column 20 at a flow rate of 1 kg/hr. In other words, the loss in recovery was 0.1%.

Comparative Example 1

N-(α-methoxyethyl)formamide was produced and purified in the same manner as in Example 1 except that the remainder of the second condensate which had not been returned to the second distillation column 40 was not returned to the storage tank 10 but was discarded.

The second column bottom liquid recovered in the recovery tank 70 was analyzed by liquid chromatography under the above conditions, and as a result, the liquid contained N-(α-methoxyethyl)formamide at 93.8%, formamide at 0.73%, N-(α-hydroxyethyl)formamide at 0.3%, and water at 0.5%.

From the above results, the proportion (recovery rate) of N-(α-methoxyethyl)formamide which passed through the first distillation column 20 and the second distillation column 40 and was then recovered was 98.6% in a case in which N-(α-methoxyethyl)formamide was distilled without returning the second condensate to the first distillation column 20 at a flow rate of 1 kg/hr, and the recovery rate decreased by 1.3% as compared with that in Example 1. In other words, the loss in recovery in Comparative Example 1 was 1.4% and thus increased by 14 times as compared with that in Example 1.

INDUSTRIAL APPLICABILITY

According to the invention, it is possible to provide a method for purifying N-(α-alkoxyethyl)formamide by which N-(α-alkoxyethyl)formamide can be purified at a high recovery rate, a method for producing high-purity N-(α-alkoxyethyl)formamide, and a device for purifying N-(α-alkoxyethyl)formamide.

EXPLANATIONS OF LETTERS OR NUMERALS

1 DEVICE FOR PURIFYING N-(α-ALKOXYETHYL) FORMAMIDE
10 STORAGE TANK
11 FIRST SUPPLY PIPE
12 FIRST REFLOW PIPE
13 FIRST SUPPLY PUMP
20 FIRST DISTILLATION COLUMN
20a COLUMN BOTTOM
20b COLUMN TOP
21 FIRST COLUMN BOTTOM OUTFLOW PIPE
22 FIRST REBOILER
23 SECOND REFLOW PIPE
24 SECOND SUPPLY PIPE
25 SECOND SUPPLY PUMP
26 FIRST OVERHEAD OUTFLOW PIPE
30 FIRST CONDENSER
31 FIRST REFLUX PIPE
32 FIRST DISCHARGE PIPE
33 SECOND DISCHARGE PIPE
34 THIRD DISCHARGE PIPE
35 FIRST VACUUM PUMP
40 SECOND DISTILLATION COLUMN
40a COLUMN BOTTOM
40b COLUMN TOP
41 SECOND COLUMN BOTTOM OUTFLOW PIPE
42 SECOND REBOILER
43 THIRD REFLOW PIPE
44 THIRD SUPPLY PIPE
45 THIRD SUPPLY PUMP
46 SECOND OVERHEAD OUTFLOW PIPE
50 SECOND CONDENSER
51 SECOND REFLUX PIPE
53 FOURTH DISCHARGE PIPE
54 FIFTH DISCHARGE PIPE
55 SECOND VACUUM PUMP
60 RETURN SECTION
61 RETURN PIPE
70 RECOVERY TANK

The invention claimed is:

1. A method for purifying N-(α-alkoxyethyl)formamide from a mixture containing the N-(α-alkoxyethyl)formamide by using a plurality of distillation columns, wherein
the plurality of distillation columns are disposed in series, and
the method comprises:
introducing a column bottom liquid of one of the distillation columns into a distillation column at a subsequent stage;
condensing an overhead efflux of the distillation column at a subsequent stage to obtain a condensate; and
returning at least a part of the condensate to a distillation column at a preceding stage.

2. The method for purifying N-(α-alkoxyethyl)formamide according to claim 1, wherein the condensation is conducted by using a condenser.

3. The method for purifying N-(α-alkoxyethyl)formamide according to claim 1, wherein at least one of the plurality of distillation columns is a packed column.

4. The method for purifying N-(α-alkoxyethyl)formamide according to claim 1, wherein a temperature of a column bottom liquid in at least one distillation column among the plurality of distillation columns is 100° C. or less.

5. The method for purifying N-(α-alkoxyethyl)formamide according to claim 1, wherein the mixture contains water and an alcohol.

6. The method for purifying N-(α-alkoxyethyl)formamide according to claim 1, wherein the condensate contains water and N-(α-alkoxyethyl)formamide.

7. A method for producing high-purity N-(α-alkoxyethyl)formamide from a mixture containing the N-(α-alkoxyethyl)formamide, water, and an alcohol by using a plurality of distillation columns, wherein
the plurality of distillation columns are disposed in series, and
the method comprises:
obtaining an overhead efflux containing an alcohol at a preceding stage and a column bottom liquid at a preceding stage in a distillation column at a preceding stage;
introducing the column bottom liquid at a preceding stage into a distillation column at a subsequent stage;
obtaining an overhead efflux containing water and N-(α-alkoxyethyl)formamide at a subsequent stage and a column bottom liquid containing N-(α-alkoxyethyl)formamide at a subsequent stage in the distillation column at a subsequent stage;
condensing the overhead efflux at a subsequent stage to obtain a condensate; and
returning at least a part of the condensate to the distillation column at a preceding stage.

8. A device for purifying N-(α-alkoxyethyl)formamide, comprising a plurality of distillation columns for distilling N-(α-alkoxyethyl)formamide-containing liquid, wherein
the plurality of distillation columns are disposed in series such that a column bottom liquid of one of the distillation columns is introduced into a distillation column at a subsequent stage, and
the device comprises a return section for returning at least a part of a condensate of an overhead efflux of the distillation column at a subsequent stage to a distillation column at a preceding stage.

9. The device for purifying N-(α-alkoxyethyl)formamide according to claim 8, comprising a condenser for condensing the overhead efflux of the distillation column at a subsequent stage.

10. The device for purifying N-(α-alkoxyethyl)formamide according to claim 9, wherein the condenser is connected to a column top of the distillation column.

11. The device for purifying N-(α-alkoxyethyl)formamide according to claim 8, wherein at least one of the plurality of distillation columns is a packed column.

* * * * *